(12) United States Patent
Ostrovsky

(10) Patent No.: US 8,506,493 B2
(45) Date of Patent: *Aug. 13, 2013

(54) IMAGING TRANSDUCER ASSEMBLY

(75) Inventor: Isaac Ostrovsky, Wellesley, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 2526 days.

This patent is subject to a terminal disclaimer.

(21) Appl. No.: 11/289,981

(22) Filed: Nov. 29, 2005

(65) Prior Publication Data

US 2006/0106314 A1 May 18, 2006

Related U.S. Application Data

(63) Continuation of application No. 10/401,901, filed on Mar. 28, 2003, now Pat. No. 7,801,094.

(51) Int. Cl.
*A61B 8/00* (2006.01)

(52) U.S. Cl.
USPC ........... 600/466; 600/407; 600/424; 600/431; 600/433; 600/435; 600/437; 600/459; 600/462

(58) Field of Classification Search
USPC ................. 600/407, 437, 585, 424, 459–471; 606/15
See application file for complete search history.

(56) References Cited

U.S. PATENT DOCUMENTS

| | | | |
|---|---|---|---|
| 4,899,757 A | 2/1990 | Pope, Jr. et al. | |
| 5,131,397 A | 7/1992 | Crowley | |
| 5,353,798 A | 10/1994 | Sieben | |
| 5,368,035 A | 11/1994 | Hamm et al. | |
| 5,386,828 A | 2/1995 | Owens et al. | |
| 5,724,978 A | 3/1998 | Tenhoff | |
| 5,782,765 A | 7/1998 | Jonkman | |
| 5,947,905 A * | 9/1999 | Hadjicostis et al. | 600/463 |
| 5,951,480 A | 9/1999 | White et al. | |
| 5,984,871 A | 11/1999 | TenHoff et al. | |
| 6,019,726 A | 2/2000 | Webb | |
| 6,024,739 A | 2/2000 | Ponzi et al. | |
| 6,190,353 B1 | 2/2001 | Makower et al. | |
| 6,233,476 B1 | 5/2001 | Strommer et al. | |
| 6,261,247 B1 | 7/2001 | Ishikawa et al. | |
| 6,283,918 B1 | 9/2001 | Kanda et al. | |
| 6,309,370 B1 * | 10/2001 | Haim et al. | 604/66 |
| 6,522,911 B1 | 2/2003 | Toida et al. | |
| 6,529,760 B2 | 3/2003 | Pantages et al. | |
| 6,801,803 B2 | 10/2004 | Vierio-Oja | |
| 2001/0029337 A1 | 10/2001 | Pantages et al. | |
| 2003/0055335 A1 | 3/2003 | Sauer et al. | |

FOREIGN PATENT DOCUMENTS

WO 9203972 A1 3/1992

* cited by examiner

*Primary Examiner* — Peter Luong
(74) *Attorney, Agent, or Firm* — Frommer Lawrence & Haug LLP; Bruce E. Black

(57) ABSTRACT

The present invention is generally directed towards an imaging transducer assembly. Generally, the imaging transducer assembly is combined with a sensor of a medical positioning system. In one aspect, the transducer assembly and the sensor share the same voltage source. In another aspect of the invention, the sensor surrounds a portion of the imaging transducer assembly, forming a housing that reinforces the assembly.

16 Claims, 6 Drawing Sheets

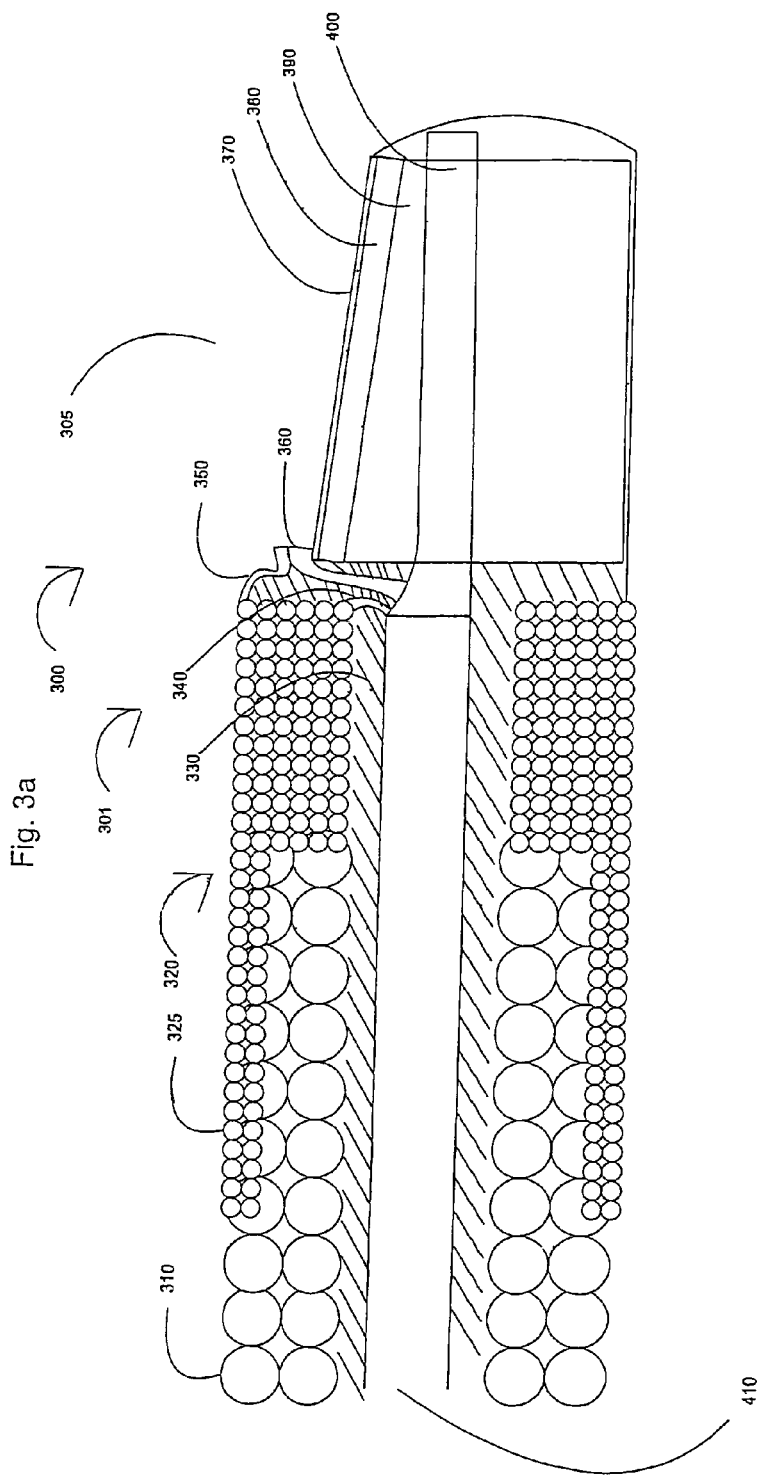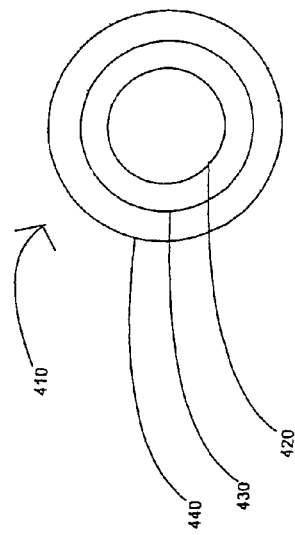
Fig. 3a
Fig. 3b

IMAGING TRANSDUCER ASSEMBLY

RELATE BACK

This application is a continuation of application Ser. No. 10/401,901 filed on Mar. 28, 2003 now U.S. Pat. No. 7,801,094, all of which is expressly incorporated herein by reference.

FIELD OF THE INVENTION

The field of the invention relates to medical imaging systems, and more particularly to an improved imaging transducer assembly.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

FIG. 1a shows an example of an imaging transducer assembly 1 known in the art. The imaging transducer 1 is typically within the lumen 60 of a guidewire (partially shown), having an outer tubular wall member 5. The imaging transducer assembly 1 includes a coaxial cable 110, having a center conductor wire 120 and an outer shield wire 140, shown in FIG. 1b. A conductive wire, having a diameter of approximately 500 microns, is wrapped around the coaxial cable 110, forming a coil, which functions as a drive shaft 10. Connected to the distal end of the drive shaft 10 is a stainless steel housing 20, which serves to reinforce the structure of the imaging transducer assembly 1. Surrounding the coaxial cable 110, within the housing 20 is a silver epoxy 30, a conductive material. Thus, the housing 20 is electrically coupled to the shield wire 140 of the coaxial cable 110 via the epoxy 30. On the distal end of the silver epoxy 140 is an insulating substance, a non-conductive epoxy 35.

On the distal end of the non-conductive epoxy 35 is a layer of piezoelectric crystal ("PZT") 80, "sandwiched" between a conductive acoustic lens 70 and a conductive backing material 90, formed from an acoustically absorbent material (e.g., an epoxy substrate having tungsten particles). The acoustic lens 70 is electrically coupled with the center conductor wire 120 of the coaxial cable 110 via a connector 40 that is insulated from the silver epoxy 30 and the backing material 90 by the non-conductive epoxy 35. The backing material 90 is connected to the steel housing 20. It is desirable for the imaging transducer assembly 1 to be surrounded by a sonolucent media. Thus, the lumen 60 of the guidewire is also filled with saline around the assembly 1. The driveshaft 10, the housing 20, and the acoustic lens 70 are exposed to the saline. During operation, the PZT layer 80 is electrically excited by both the backing material 90 and the acoustic lens 70. The backing material 90 receives its charge from the shield wire 140 of the coaxial cable 110 via the silver epoxy 30 and the steel housing 30, and the acoustic lens 70, which may also be silver epoxy, receives its charge from the center conductor wire 120 of the coaxial cable 110 via the connector 40, which may be silver epoxy as well.

Turning to FIG. 1c, the imaging transducer assembly 1 can be depicted as a simple electric circuit having a voltage source 150, two terminals, A and B, a load 81 caused by the saline filled in the lumen 60, and the PZT load 80. The saline load 81 and the PZT load 80 are charged by the voltage source 150 via the two terminals, A and B, representing the shield wire 140 and the center conductor wire 120 of the coaxial cable 110, respectively. In addition, transducer control circuitry (not shown), which may include a signal processor to handle imaging signals, may also be coupled with the transducer assembly 1.

The imaging transducer is an effective tool for obtaining the cross-sectional image of a blood vessel. However, in some instances, it may be desirable to obtain more information, such as a three-dimensional longitudinal profile of the same blood vessel in addition to the cross-sectional image. Accordingly, an improved imaging transducer assembly would be desirable.

SUMMARY OF THE INVENTION

The improved imaging device is intended for use within the lumen of a blood vessel. Generally, the imaging transducer assembly is combined with a sensor of a medical positioning system.

In one embodiment, the imaging transducer assembly and the sensor may be electrically charged using a first and second terminal. The imaging transducer assembly may be coupled with a coaxial cable having a center wire and an outer wire, wherein one of the first and second terminals is coupled with the center wire and the other of the first and second terminal is coupled with the outer wire. Further, at least one of the first and second terminals is insulated from any sonolucent media in contact with the imaging transducer assembly. Further, the sensor surrounds the imaging transducer assembly, forming a housing structure to reinforce the assembly.

In another embodiment, a method includes obtaining the cross-sectional image of a blood vessel and at substantially the same time, obtaining the longitudinal profile of the same blood vessel.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. More

FIG. 1b is a cross-sectional view of the coaxial cable within the prior art imaging transducer assembly of FIG. 1a.

FIG. 1c is a simplified diagram of an electrical circuit formed by the prior art imaging transducer assembly of FIG. 1a.

FIG. 3a is cross-sectional side view of an imaging transducer assembly in accordance with an exemplary embodiment of the present invention.

FIG. 3b is a cross-sectional view of a coaxial cable within the imaging transducer assembly of FIG. 3a.

FIG. 3c is a simplified diagram of an electrical circuit formed by the imaging transducer assembly of FIG. 3a.

DETAILED DESCRIPTION OF THE PREFERRED EMBODIMENTS

Described below is an improved imaging transducer assembly.

Figure 1A:
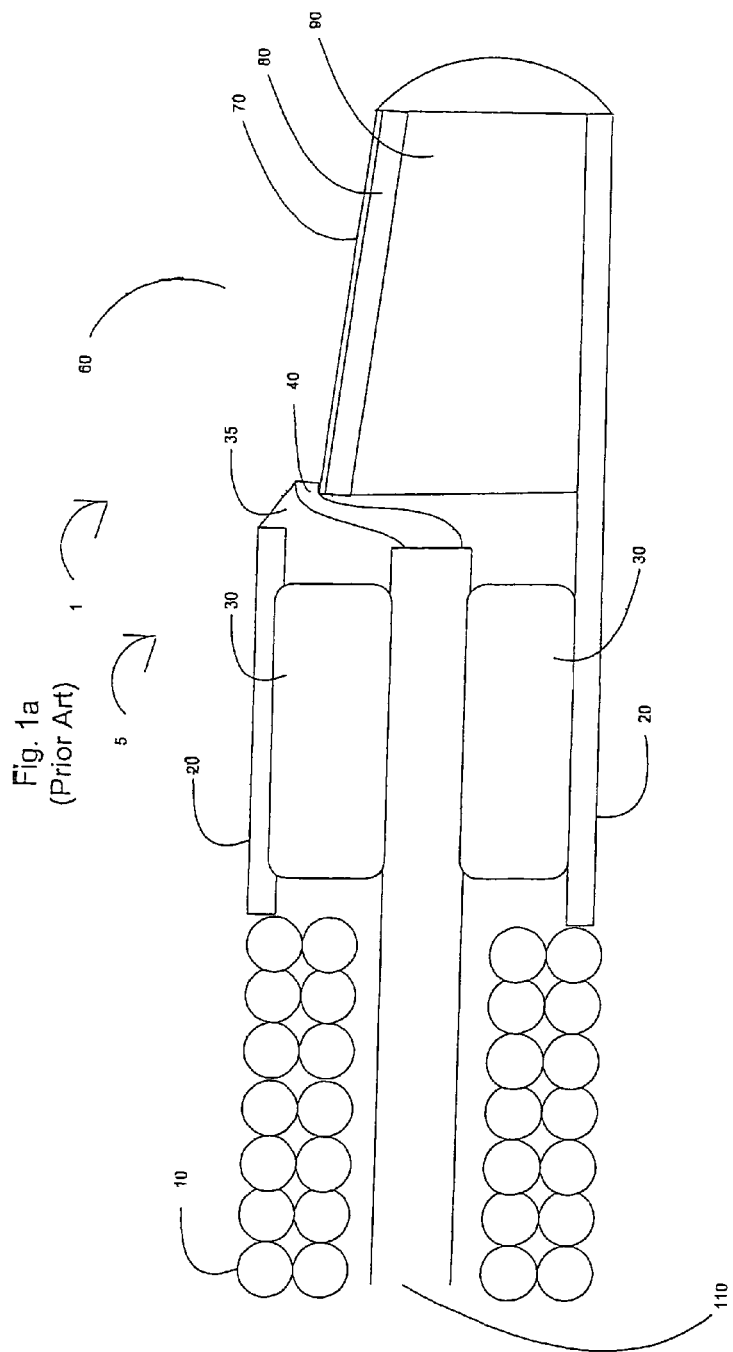
- FIG. 1a is a cross-sectional side view of an imaging transducer assembly known in the art.
Figure 1C:
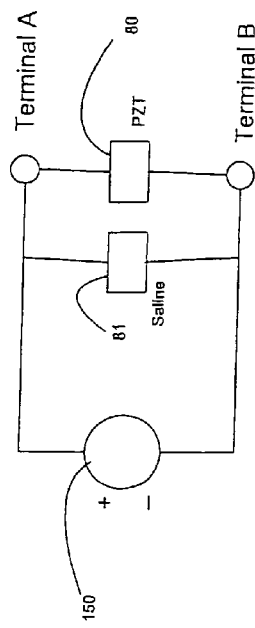
Figure 1B:
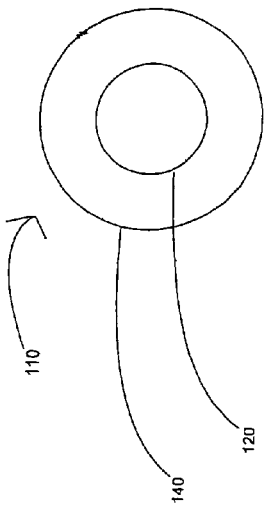
Figure 2A:
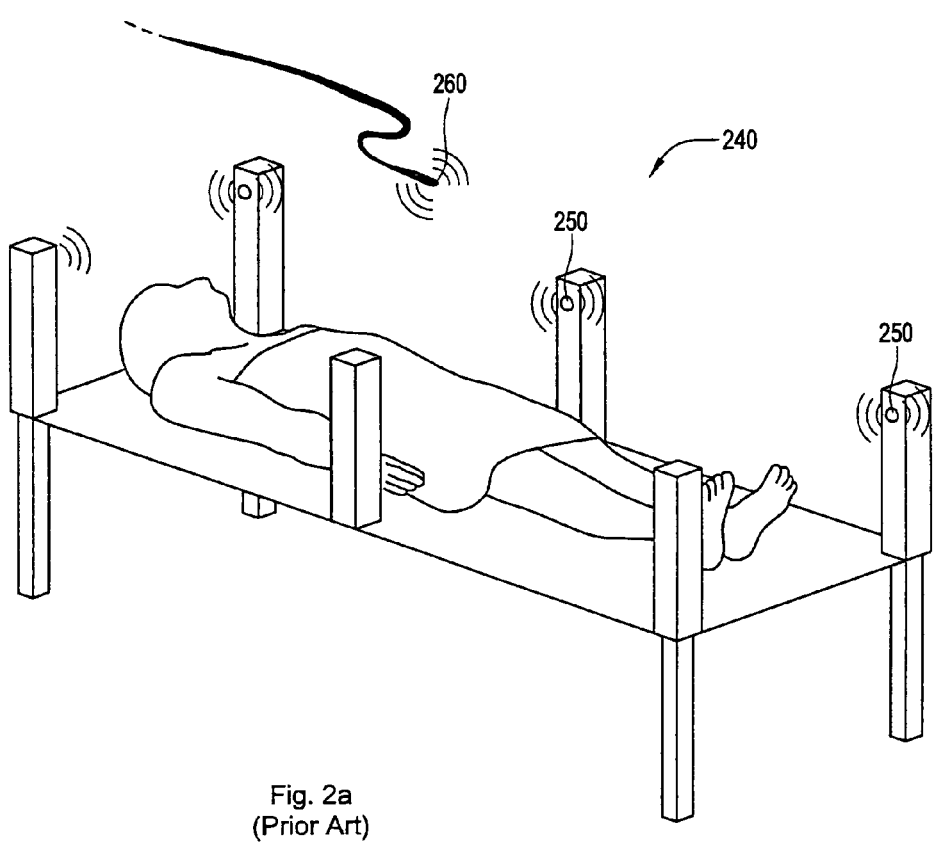
FIG. 2a is an illustration of a prior art medical positioning system.

In some instances, it may be desirable to be able to obtain not only the cross-sectional image of a blood vessel, but also information such as the three-dimensional longitudinal profile of the same blood vessel. One approach in obtaining such additional information is to use a medical positioning system, which is generally known in the art. Turning to FIG. 2a, a prior art medical positioning system 240 is illustrated. The system 240 generally includes a plurality of transmitter and/or receiver nodes 250 that may be arranged around a patient. For instance, the nodes 250 may be arranged on a framework of towers that surround a patient. The system 240 further includes one or more sensors 260, which are configured to send and/or receive electro-magnetic, or electromechanical, signals to and/or from the transmitter/receiver nodes 250.

A sensor 260, coupled with a guidewire (partially shown), may be placed within the blood vessel of a patient's body. The signals exchanged between the sensor 260 and the nodes 250 function as navigational signals which, as can be appreciated by one of ordinary skill in the art, may be used to determine the position of the sensor 260 within the patient's body. In other words, the sensor 260 transmits navigational signals to the nodes 250, and a processor (not shown) coupled with the nodes 250 determines the position of the sensor 260 based on the signals received by the nodes 250. Alternatively, or in addition, the nodes 250 may send navigational signals to the sensor 260, and a processor (not shown) coupled with the sensor 260 determines the position of the sensor 260 within the patient's body based on the signals sent by the nodes 250. The medical positioning system 240 can track and record the position of the sensor 260 as it is moved throughout a patient's blood vessel, thus providing a longitudinal profile of the blood vessel.

Figure 2B:
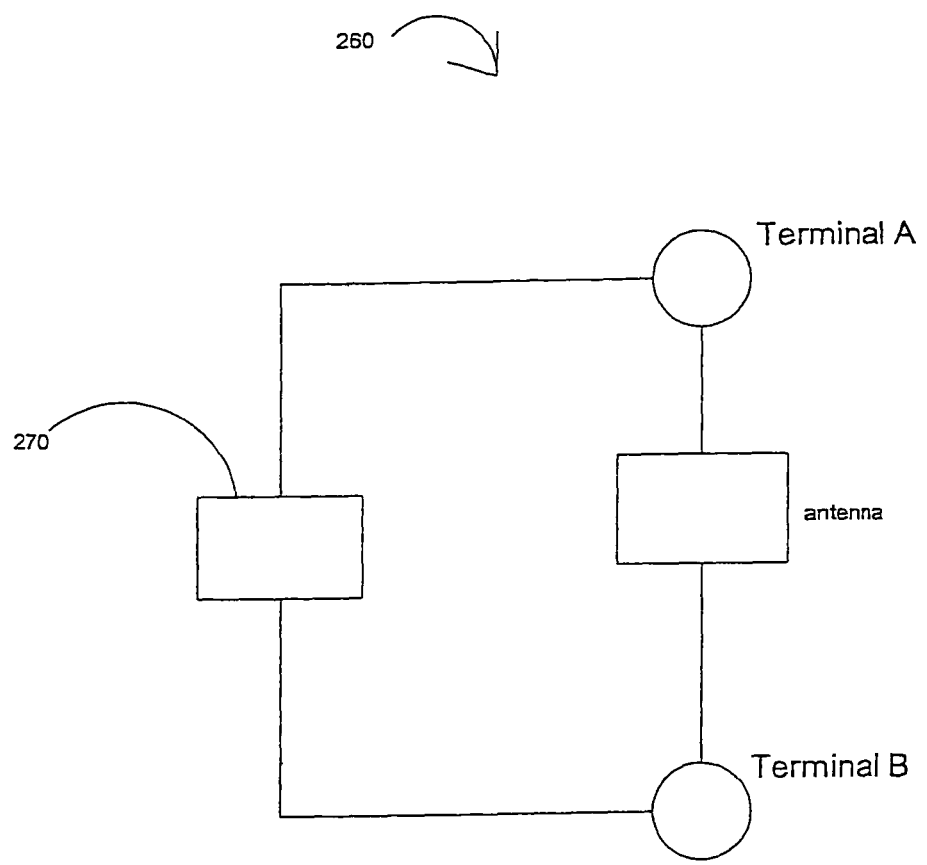
FIG. 2b is a simplified diagram of an electrical circuit formed by a sensor of a prior art medical positioning system.

Turning to FIG. 2b, the sensor 260 is depicted as a simplified electrical circuit having two terminals, A and B, an "antenna" load, and a load 270. The antenna is the portion of the sensor 260 where a substantial amount of the navigational signals are sent and/or received. If the sensor 260 is configured to send electromagnetic signals to the nodes 250, then to facilitate the electromagnetic broadcast, the load 270 may be a voltage source 270, which charges the antenna via the terminals A and B. Alternatively, if the sensor 260 is configured to receive electromagnetic signals from the nodes 250, then the load 270 may be sensor circuitry, which may include a signal processor (not shown) to handle navigational signals.

Figure 3C:
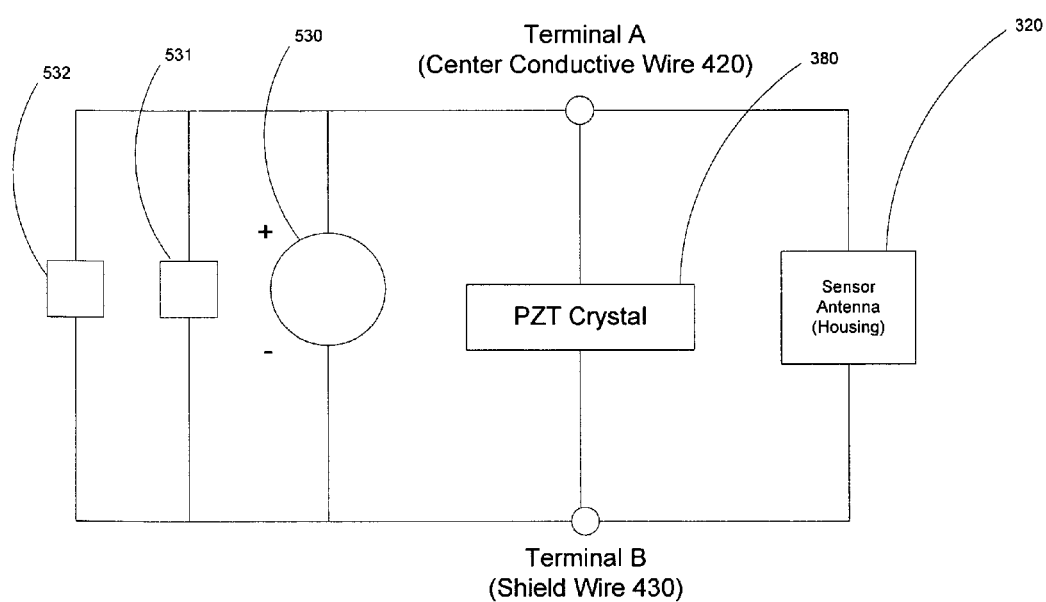

In one example preferred embodiment of the improved imaging transducer assembly shown in FIGS. 3a and 3b, a sensor of a medical positioning system may be combined with an imaging transducer to form a transducer/sensor assembly 300. Turning to FIG. 3a, a cross-sectional side view of a transducer/sensor assembly 300 is shown in a lumen 305 of the distal portion of a guidewire or catheter assembly (partially shown) having an outer tubular wall 301. The transducer/sensor assembly 300 includes a coaxial cable 410, having a center conductor wire 420, and an outer shield wire 430, as shown in FIG. 3b. The center conductor wire 420 is insulated from the outer shield wire 430. In addition, the shield wire 430 is surrounded by an insulating jacket 440. It should be noted that numerous alternative cable configurations may be used; for example, a cable having "twisted pair" wires may be used instead of a coaxial cable.

Turning back to FIG. 3a, surrounding the coaxial cable 410 is a layer of insulating material, such as a non-conductive epoxy 330. Surrounding the epoxy 330 is a drive shaft 310, which is a conductive wire wound around the epoxy 330/coaxial cable 350 to form a first coil shape 310. Preferably, the conductive wire is stainless and has a diameter of approximately 500 microns. Thus, the coaxial cable 350 is conductively insulated from the drive shaft 310.

The distal end of the transducer/sensor assembly 300 includes an electrically conductive backing material 390, having a top, bottom and center, which may be formed from an acoustically absorbent material (for example, an epoxy substrate having tungsten particles). The center of the backing material 390 surrounds a shield pellet 400, which is electrically coupled to the shield wire 430 at the distal end of the coaxial cable 410. The top of the backing material 390 is coupled to the bottom of a layer of piezoelectric crystal (PZT) 380. The top of the PZT layer 380 is coupled to a conductive acoustic lens 370, which may include silver epoxy. The acoustic lens 370 is electrically coupled to the center conductor wire 420 of the coaxial cable 410 via a connector 360, which may include silver epoxy, surrounding the non-conductive epoxy 330 such that the connector 360 is insulated from the backing material 390.

The transducer/sensor assembly 300 further includes a sensor 320 of a medical positioning system. The "antenna" portion of the sensor 320 is an insulated conductive wire 325. The wire 325 may also have magnetic qualities. The wire 325 is tightly wrapped around a portion of the distal end of the coaxial cable 410 and non-conductive epoxy 330, and is also tightly wrapped around the distal end of the drive shaft 310, forming a second coil shape. The second coil shape desirably provides an inductance for the antenna portion of the sensor 320 when charged to increase its ability to send and receive electromagnetic signals. The second coil shape also serves as a housing to reinforce the transducer/sensor assembly 300. However, it should be noted that the antenna portion of the sensor 320 may have a variety of other shapes and configurations. For example, the antenna portion of the sensor 320 may be a solid structure. The wire 325 is preferably copper and approximately 10 microns in diameter. The small diameter of the wire 325 allows the sensor 320 to have a small impact on the dimensions of the transducer/sensor assembly 300, thus allowing the transducer/sensor assembly 300 to still work within the lumen 305 of the guidewire or catheter assembly.

The two ends of the wire 325 are terminals that receive an electric charge. One end 350 of the wire 325 is coupled to the connector 360 that electrically couples the acoustic lens 370 with the center conductor wire 420 of the coaxial cable 410. The other end 340 of the wire 325 is coupled to the shield wire 430 of the coaxial cable 410, surrounded and insulated from the drive shaft 310 and the connector 360 by the non-conductive epoxy 330.

To facilitate the operation of the imaging transducer portion of the transducer/sensor assembly 300, the lumen 305 of the guidewire or catheter assembly is preferably filled with a sonolucent media, such as saline. It is desirable to have at least one of the ends 350, 340 of the wire 325 of the sensor 320 be insulated from the saline within the lumen 305 because if both ends, 350 and 340, were exposed to the saline, the semiconductive nature of the saline might shunt the ends, 350 and 340, thus undesirably "shorting out" the antenna of the sensor 320, and/or affecting the signal-to-noise ratio of the navigational signals. In light of this, the transducer/sensor assembly 300 preferably has one end 340 of the wire 325 of the sensor insulated from the drive shaft 310, backing material 390, connector 360, and saline by the non-conductive epoxy 330. Further, the coil portion of the wire 325 is also insulated from the driveshaft 310 and the saline in the lumen 305 by a non-conductive material. The other end 350 of the wire 325, however, may be exposed to the saline.

During the operation of the transducer/sensor assembly 300, the PZT crystal 380 is electrically excited by both the backing material 390, charged through the shield wire 430, and the acoustic lens 370, charged through the center conductor wire 420. In addition, the antenna portion 325 of the sensor 320 is also charged by the shield wire 430 and the center conductor wire 420. If the sensor 320 is configured to send electromagnetic signals to nodes of a medical positioning system (not shown), then the charge may facilitate a broadcast. However, if the sensor 320 is configured to receive electromagnetic signals from one or more nodes of a medical positioning system (not shown), then separate circuitry including a signal processor may be used to filter and extract the desired electromagnetic signals. Thus, turning to FIG. 3c, the assembly 300 is depicted as a simplified electric circuit having a voltage source 530, the load of the PZT layer 380, the load of the antenna portion 325 of the sensor 320, which is in parallel with the load of the PZT layer 380, sensor circuitry 531, which may include a signal processor (not shown) to receive and process electromagnetic signals, i.e., navigational signals, from the sensor 320, as would be known to a person of skill in the art, transducer circuitry 532, which may also include a signal processor (not shown) to process imaging signals from the imaging transducer, and terminals A and B. Terminals A and B represent the center conductor wire 420 and the shield wire 430 of the coaxial cable 410, respectively. Other features and circuits may also be added as desired.

Figure 4:
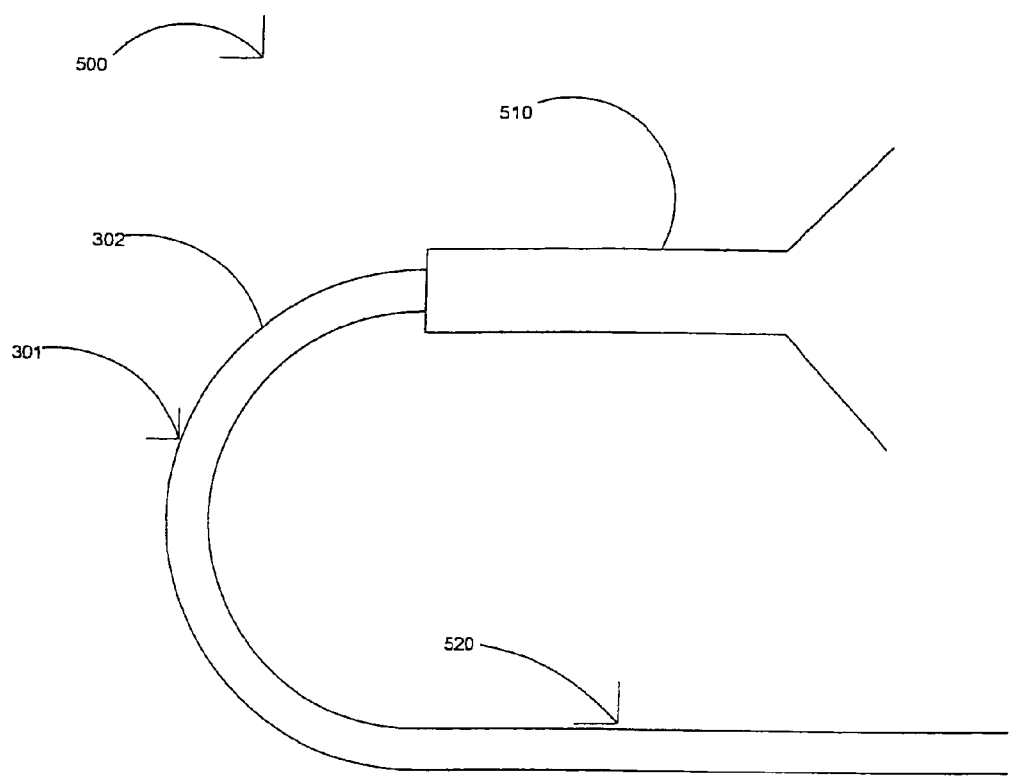
FIG. 4 is a partial cross-sectional side view of a catheter in accordance with an exemplary embodiment of the present invention.

Turning to FIG. 4, the transducer/sensor assembly 300 may be placed in a distal portion 520 of a guidewire 500. The guidewire 500 may comprise a guidewire body 302 in the form of a flexible, elongate tubular member, having an outer wall 301. The guidewire body 302 may be formed of any material known in the art including nitinol hypotube, metal alloys, composite materials, plastics, braided polyimide, polyethylene, peek braids, stainless steel, or other superelastic materials.

The length of the guidewire 500 may vary depending on the application. In a preferred embodiment, the length of the guidewire 500 is between 30 cm and 300 cm. A catheter (not shown) may be configured to use several different diameters of guidewires 500. For example, the guidewire 500 may have a diameter of 0.010, 0.014, 0.018, or 0.035 inches. Typically, the diameter of the guidewire 500 is uniform.

A proximal portion 510 of the guidewire 500 may be adapted to connect to circuitry (not shown) that processes imaging signals from the imaging transducer and/or circuitry (not shown) that processes navigational signals from the sensor 320., such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices, but can be used on any design involving imaging devices in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An imaging catheter having distal and proximal ends and a lumen, comprising:
   a coaxial cable comprising a center wire, an outer shield, and a distal end;
   an imaging transducer assembly located within the lumen of a distal portion of the catheter, the imaging transducer assembly including an imaging transducer; and
   a sensor adapted to communicate with a medical positioning system, wherein the sensor and the imaging transducer are each electrically coupled, in a parallel electrical configuration with respect to each other, to the center wire and the outer shield at the distal end of the coaxial cable.

2. The imaging catheter of claim 1, wherein the imaging transducer assembly comprises an acoustic lens coupled with a layer of piezoelectric crystal, the piezoelectric crystal being coupled with a backing material.

3. The imaging catheter of claim 2, wherein the backing material comprises a tungsten material.

4. The imaging catheter of claim 1, wherein the catheter includes a driveshaft proximal to the imaging transducer assembly, and the sensor comprises a conductive material surrounding the driveshaft to form a housing around the driveshaft.

5. The imaging catheter of claim 2, wherein the sensor includes an insulated conductive wire wrapped around the driveshaft to form a coil shape.

6. The imaging catheter of claim 1, wherein the sensor includes an antenna portion having first and second terminals.

7. The imaging catheter of claim 6, wherein at least one of the first and second terminals is insulated from the lumen.

8. The imaging catheter of claim 6, wherein the imaging transducer and the sensor share the first and second terminals.

9. The imaging catheter of claim 6, wherein the imaging transducer assembly has a first and second transducer terminal, the first transducer terminal being coupled to the center wire of the coaxial cable and the second transducer terminal being coupled to the outer shield of the coaxial cable.

10. The imaging catheter of claim 1, further comprising:
a non-conductive epoxy surrounding the coaxial cable; and
a drive shaft surrounding the non-conductive epoxy;
wherein the sensor comprises an insulated conductive wire wrapped around at least a distal portion of the drive shaft, the conductive wire having a first and second wire terminal, wherein at least one of the first and second wire terminals is coupled to the outer shield of the coaxial cable and the other of the first and second wire terminals is coupled to the center wire of the coaxial cable; and
wherein the imaging transducer assembly comprises:
a backing material coupled to the outer shield of the coaxial cable;
a piezoelectrical crystal coupled to the backing material; and
an acoustic lens coupled to the piezoelectrical crystal and coupled to the center wire of the coaxial cable.

11. A medical imaging system comprising:
a medical positioning system; and
an imaging device adapted to be inserted into a lumen of a body, the imaging device including:
the imaging catheter of claim 1.

12. The medical imaging system of claim 11, wherein the imaging transducer assembly comprises an acoustic lens coupled with a layer of piezoelectric crystal, the piezoelectric crystal being coupled with a backing material.

13. The medical imaging system of claim 11, wherein the catheter includes a driveshaft proximal to the imaging transducer assembly, and the sensor comprises a conductive material surrounding the driveshaft to form a housing around the driveshaft.

14. The medical imaging system of claim 11, wherein the sensor includes an antenna portion having first and second terminals.

15. The medical imaging system of claim 14, wherein the imaging transducer and the sensor share the first and second terminals.

16. The medical imaging system of claim 14, wherein the imaging transducer assembly has a first and second transducer terminal, the first transducer terminal being coupled to the center wire of the coaxial cable and the second transducer terminal being coupled to the outer shield of the coaxial cable.

\* \* \* \* \*

UNITED STATES PATENT AND TRADEMARK OFFICE
CERTIFICATE OF CORRECTION

PATENT NO. : 8,506,493 B2
APPLICATION NO. : 11/289981
DATED : August 13, 2013
INVENTOR(S) : Isaac Ostrovsky Page 1 of 1

It is certified that error appears in the above-identified patent and that said Letters Patent is hereby corrected as shown below:

On the Title Page, Item (73) insert --Assignee: Boston Scientific SciMed, Inc.--

Signed and Sealed this
Tenth Day of December, 2013

Margaret A. Focarino
*Commissioner for Patents of the United States Patent and Trademark Office*